(12) United States Patent
North et al.

(10) Patent No.: US 6,235,537 B1
(45) Date of Patent: May 22, 2001

(54) METHODS FOR WASHING CELLS

(75) Inventors: Howard L. North, Los Gatos; Harvey Schulte, Los Altos; Eric Chase, Walnut Creek, all of CA (US)

(73) Assignee: Cytek Corporation, Fremont, CA (US)

( * ) Notice: Subject to any disclaimer, the term of this patent is extended or adjusted under 35 U.S.C. 154(b) by 0 days.

(21) Appl. No.: 09/118,495

(22) Filed: Jul. 17, 1998

Related U.S. Application Data

(63) Continuation-in-part of application No. 08/677,449, filed on Jun. 20, 1996, now Pat. No. 5,840,253.

(51) Int. Cl.[7] .................................................. G01N 1/18
(52) U.S. Cl. ........................ 436/177; 436/174; 436/178; 436/180; 436/183; 494/37
(58) Field of Search ........................ 435/2, 372; 436/177, 436/174, 180, 183; 210/782, 787, 789; 530/427, 412; 494/37

(56) References Cited

U.S. PATENT DOCUMENTS

| | | | |
|---|---|---|---|
| 3,465,957 | * | 9/1969 | Brandt ..................................... 494/16 |
| 3,722,790 | * | 3/1973 | Natelson ................................ 494/11 |
| 3,858,795 | * | 1/1975 | Joyce ..................................... 494/37 |
| 3,877,634 | * | 4/1975 | Rohde et al. ............................ 494/1 |
| 4,058,252 | * | 11/1977 | Williams ................................ 233/14 |
| 4,639,242 | * | 1/1987 | Babson .................................. 494/37 |
| 4,668,214 | * | 5/1987 | Reeder ................................... 494/37 |
| 5,030,341 | * | 7/1991 | McEwen et al. ....................... 210/94 |
| 5,084,240 | * | 1/1992 | Babson .................................. 422/72 |
| 5,215,376 | * | 6/1993 | Schulte ................................ 366/348 |
| 5,275,731 | * | 1/1994 | Jahn ..................................... 210/518 |
| 5,316,726 | * | 5/1994 | Babson et al. ......................... 422/65 |
| 5,405,308 | * | 4/1995 | Headley ................................ 494/67 |
| 5,478,479 | * | 12/1995 | Herrig .................................. 210/745 |
| 5,529,933 | * | 6/1996 | Young et al. .......................... 436/10 |
| 5,730,938 | * | 3/1998 | Carbonari et al. ..................... 422/64 |
| 5,840,253 | * | 11/1998 | Chase et al. ........................... 422/63 |

* cited by examiner

Primary Examiner—Arlen Soderquist
(74) Attorney, Agent, or Firm—Thomas Schneck; David M. Schneck

(57) ABSTRACT

An apparatus and method are disclosed to wash blood cells in a discrete manner that is compatible with automated sample preparation systems. The test tube containing the cells to be washed is mounted on a rotatable spindle. The spindle includes central passageways for the introduction of wash fluid and air into the test tube, and radial exit passageways at the bottom of the spindle. The test tube is first spun about its vertical axis to centrifuge cells against the inner wall of the test tube. A vacuum is then applied to the exit passageways so cell supernatant is aspirated out through the exit passageways. Wash fluid is then introduced into the test tube, and aspirated out through the exit passageways, thereby washing the cells. Rotational acceleration and deceleration of the test tube then resuspends the cells in wash fluid.

12 Claims, 3 Drawing Sheets

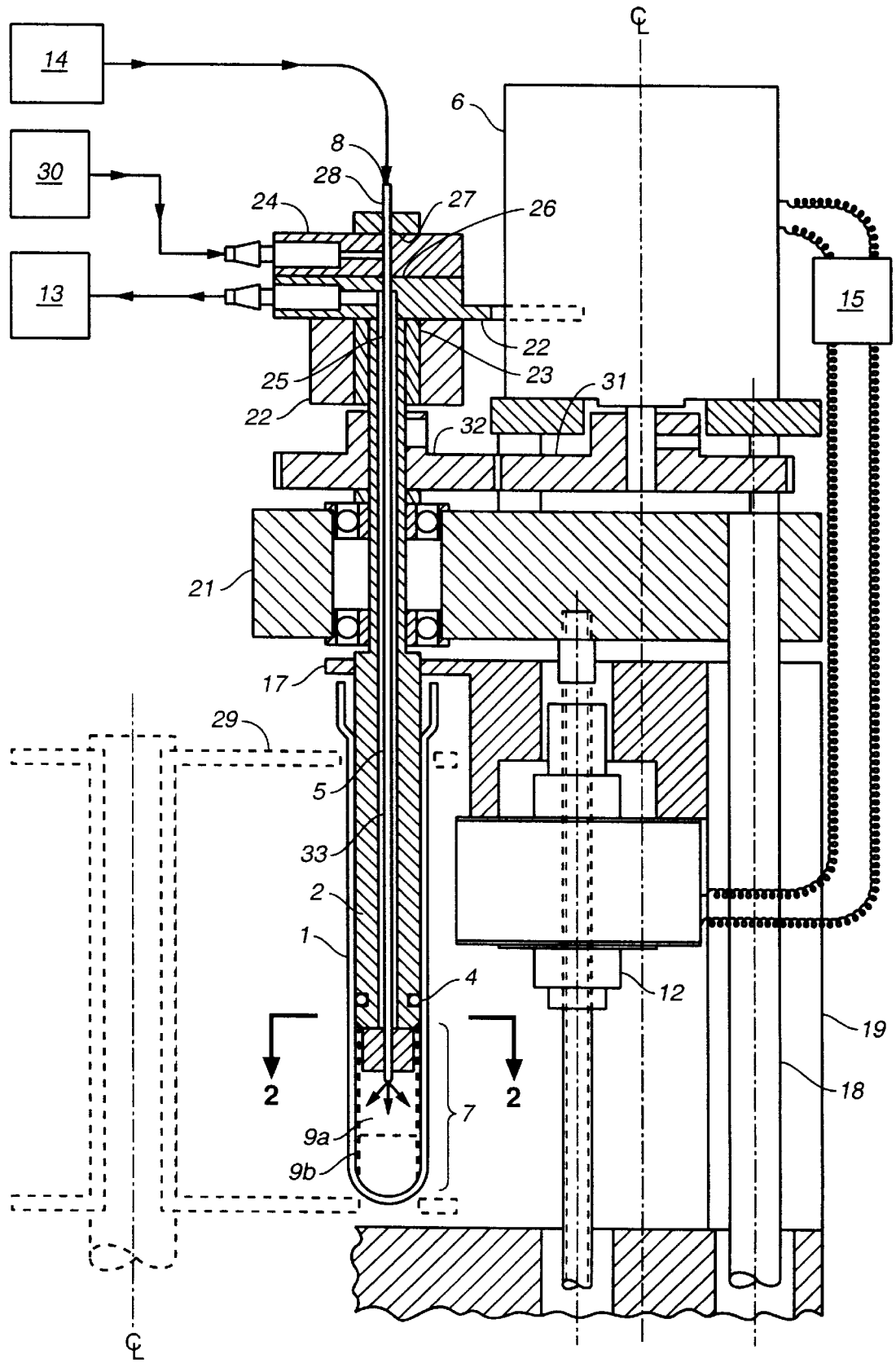
FIG._1

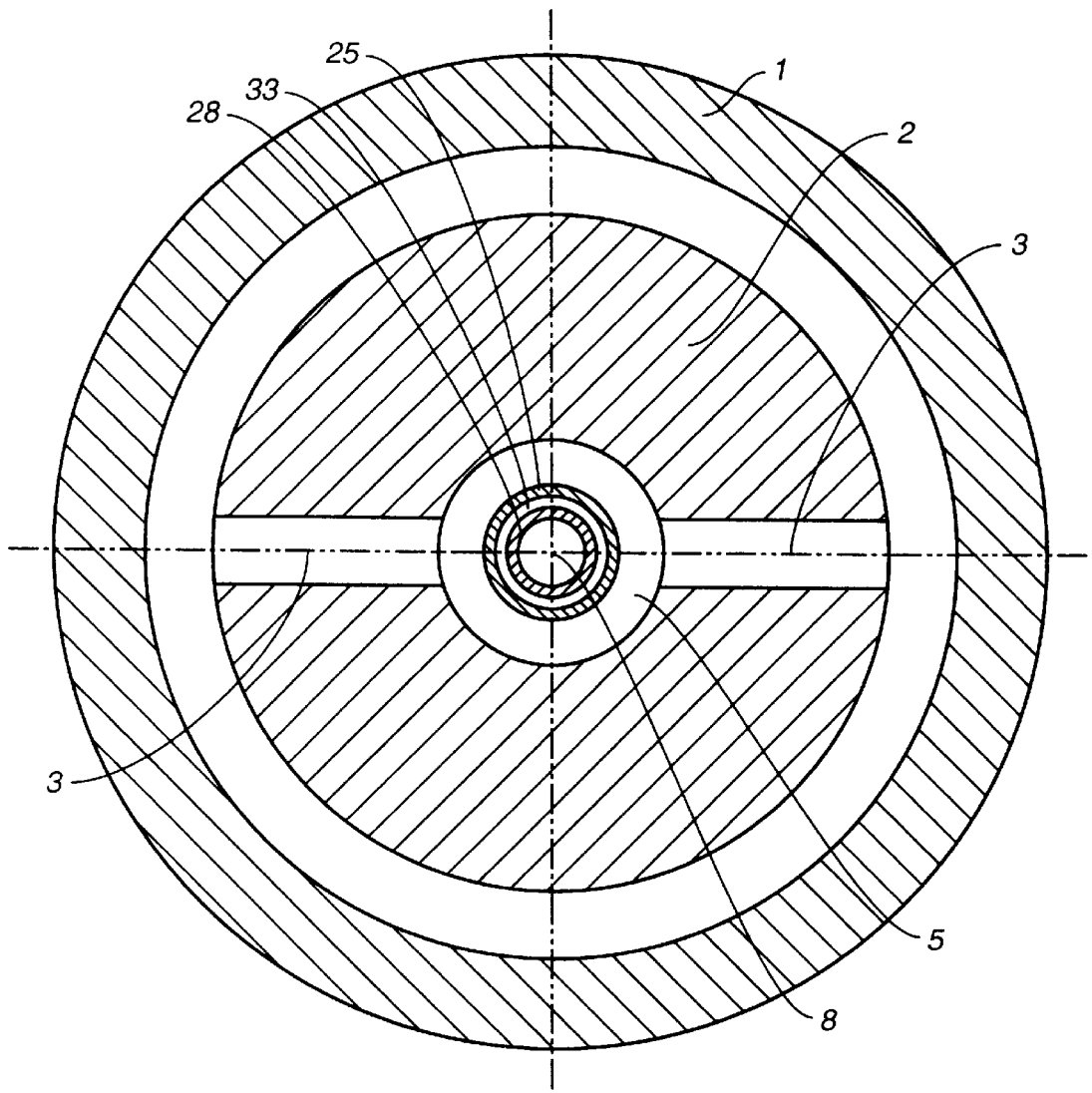
FIG._2

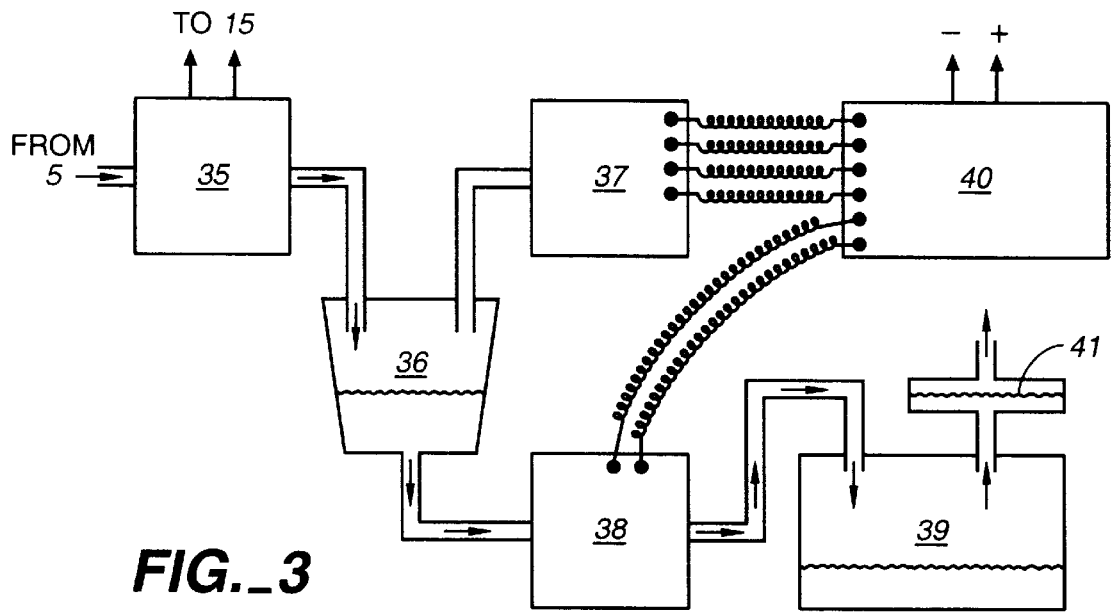
FIG._3
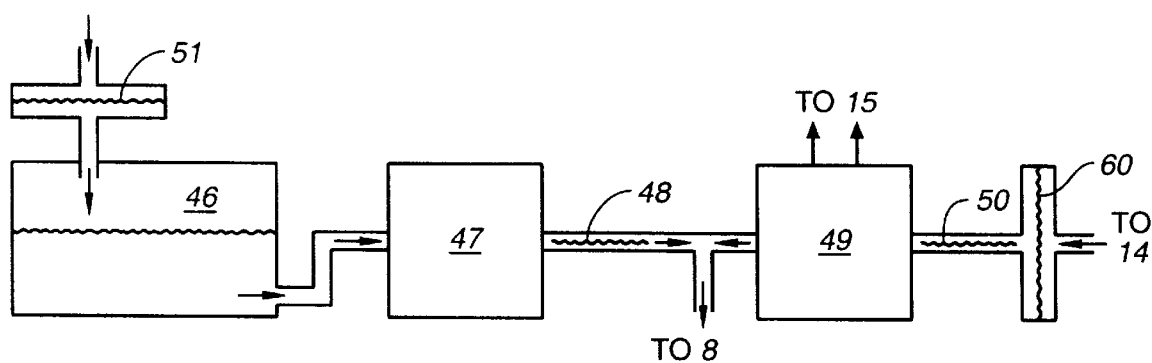
FIG._4
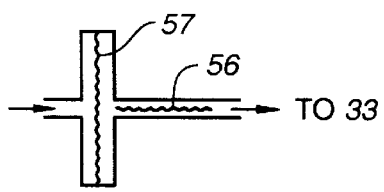
FIG._5

METHODS FOR WASHING CELLS

RELATED APPLICATIONS

This application is a continuation-in-part of prior application Ser. No. 08/667,449, filed Jun. 20, 1996, now U.S. Pat. No. 5,840,253, entitled "Cell Wash Apparatus and Method".

FIELD OF THE INVENTION

This invention relates to a method and apparatus for washing biological cells that is compatible with automated equipment.

BACKGROUND OF THE INVENTION

Many procedures involving the preparation of biological cells for analysis require that unreacted reagents and cellular debris be separated from the cells of interest. Traditionally batch centrifugation has been the method of choice to perform this separation. However, batch centrifugation is not readily adaptable to automated sample preparation systems.

Most automated sample preparation equipment utilize circular or rectangular arrays of disposable test tubes. The test tubes are transported to appropriate positions so various operations can be performed sequentially and discretely on each test tube. In many sample preparation procedures, the time between discrete operations must be carefully controlled to obtain reliable and reproducible results. However, the operation of cell washing by centrifugation, as it is practiced in the art, is a batch operation. This batch operation cannot be performed sequentially and discretely on each test tube. The presence of a batch operation by definition disrupts the timing of the discrete operations which precede and follow the batch operation.

Batch centrifugations require substantially equal volumes of liquid in each tube to balance the centrifuge rotor, which may not always be desirable in an automated sample preparation system.

Batch centrifugations require rotational alignment of the centrifuge rotor with the loading/unloading system which introduces additional complexity into the centrifuge drive. Samples also require positive sample identification after centrifugation to verify rotational alignment was achieved.

Lastly, the centrifuge rotor and loading/unloading apparatus increases the size, weight and complexity of the system.

In spite of these limitations, automated sample handling systems that utilize batch centrifugation do exist. The ASHS system, marketed by Automed, automates the loading and unloading of conventional centrifuges using robotics; however such systems are large and costly, and only suitable for high volume laboratories.

Another category of instruments has been developed for blood washing and processing, as described in U.S. Pat. Nos. 5,405,308, 4,983,158, 4,668,214, 4,300,717, and 4,086,924. Generally these instruments consist of a bowl assembly with a central feed tube to introduce blood or wash solution to the bowl, feed tube and seal assembly which provide an input feed line to the bowl and an output line from the bowl, and a core assembly that imparts angular velocity to the incoming fluid. These instruments are not suitable for cell washing in automated sample preparation equipment because they require specialized bowl/core structures to enhance the processing of large quantities (ca 500 ml) of undiluted blood.

A number of companies market automatic cell washers. One such system, the Centra-W Automatic Cell Washer marketed by IEC, automate the aspiration of supernatant and addition of dilutent, but still require manual loading and unloading of the sample containers into and from the centrifuge rotor. Consequently, these types of instruments are not compatible with automated sample preparation equipment.

It would be desirable to have a method and apparatus to wash cells that are compatible with automated sample preparation equipment. Such a method and apparatus should operate on each sample individually so it can be synchronized with the other discrete operations performed on the samples.

It would also be desirable to have an apparatus that could be implemented as a discrete processing station on the periphery of a carousel or linear track sample preparation system.

Furthermore, it would be desirable to perform the wash step in the same disposable test tubes commonly used in automated sample preparation and analysis equipment.

It would also be desirable for the cell washer to effectively wash out the undesired cellular debris and unreacted reagents, and to concentrate the desired cells.

Lastly, it would be desirable to have the cell washer apparatus operate without an elaborate system to transport the sample containers to and from the cell washing apparatus.

SUMMARY OF THE INVENTION

The invention described herein provides an improved apparatus and method for removing debris and unbound reagents from cellular suspensions contained in disposable test tubes. The cell washer invention can be implemented into a variety of sample processing systems by a variety of suitable handling system embodiments familiar to those skilled in the art.

A disposable test tube containing the cell suspension to be washed is rotated about its longitudinal center line at speeds sufficient to force the cell suspension up the inner wall of the test tube. This film, typically less than a millimeter thick, is retained by an o-ring near the end of a spindle assembly concentric with the test tube. The o-ring also transfers torque from the spindle to the test tube to rotate it.

After a few seconds of rotation, the larger, more dense cells will migrate radially to the inner wall of the test tube under the action of centrifugal forces. At this time, a cell compatible washing fluid is delivered to the bottom of the test tube from an external reservoir. This wash fluid displaces the fluid containing smaller and less dense cells, cellular debris, and unbound reagent upwards, through radial passageways in the spindle, and out through suitable passages to an external waste reservoir. Wash fluid thus displaces and removes the unwanted supernatant cell suspension fluid and thus effects a washing of the cells. This process continues until the desired degree of cell washing is achieved. The wash fluid and waste fluids may be moved by suitable pumps which may produce a vacuum inside of the test tube. In the preferred embodiment described a pump producing a vacuum is used because it is a simple system and allows easy introduction and removal of air and washing fluid. The annular outflow passage in the spindle assembly has an outer diameter which in conjunction with the test tube inner diameter establishes the radial thickness of the cell suspension fluid. The final suspension volume may be controlled by the final rotational speed of the spindle. If the rotational speed is not decreased at the end of the wash cycle, the final suspension volume is represented by the annular volume between the outer diameter of the spindle. If the rotational speed of the spindle is reduced while continuing to introduce wash fluid, the reduction in rotational speed causes the wash fluid to assume a parabolic shape, thus increasing the final suspension volume. In this manner, the final suspension volume of the sample may be controlled.

The sedimentation velocity for spherical shapes is related to the difference in density of the particle and the surrounding fluid, the particle diameter, the fluid viscosity, and the particle acceleration by Stokes Equation. For irregular shapes, the density, shape and size of the particle and the viscosity of the surrounding fluid and the centrifugal forces determines the sedimentation velocity.

After the cells are adequately washed, and the resuspension volume has been established, the wash fluid flow is stopped. Then the drive motor is rapidly stopped by braking, either mechanically or electrically. Dynamic braking of a permanent magnet field direct current motor is used in the preferred embodiment because it is simple, convenient, and does not add parts which can wear out. The rapid stopping of the test tube rotation causes the fluid inside the test tube to continue rotating which washes over the cells at the test tube inner wall, which in turn resuspends the cells. Not all cells may be resuspended by a single rapid stopping of the test tube rotation, so the test tube may be rotated and stopped several times to increase cell recoveries. Also, the use of a cell compatible surfactant may be used in the wash fluid to inhibit cell sticking to the test tube.

At this point, cell washing and suspension are complete. Vacuum inside the test tube is released, and the spindle is disengaged from the test tube. The cell washer is then ready for engagement with the next test tube for washing.

BRIEF DESCRIPTION OF DRAWINGS

FIG. 1 is a cross sectional view of the cell washer, showing a test tube mounted on the apparatus.

FIG. 2 is a cross sectional view along line 2—2 of FIG. 1.

FIG. 3 illustrates the vacuum system of the present invention. This Figure is an expanded view of item 13 shown in FIG. 1.

FIG. 4 illustrates the wash fluid supply system of the present invention. This Figure is an expanded view of item 14 shown in FIG. 1.

FIG. 5 illustrates the air supply system of the present invention.

This Figure is an expanded view of item 30 shown in FIG. 1.

DESCRIPTION OF PREFERRED EMBODIMENTS

Referring to FIG. 1, the cell washing cycle begins when the carousel 29 brings test tube 1 containing a cell suspension to be washed into position directly below cell washer spindle 2. Control system 15 then causes spindle 2 to be lowered by actuator 12. Spindle support 21 and guide rods 18 in guide housing 19 couple the linear motion of actuator 12 to spindle 2. Spindle 2 is lowered such that o-ring 4 makes sealing contact with the inner wall of test tube 1, and the end of spindle 2 is at the desired height above the bottom of test tube 1. By virtue of the friction between o-ring 4 and test tube 1, actuator 12 lifts test tube 1 a small distance out of carousel 29. Control system 15 then causes motor 6 to rotate spindle 2 and test tube 1 via gears 31 and 32 at a speed such that the cell suspension rapidly forms an annular cylinder of liquid with an inner diameter located at 9a. O-ring 4 prevents the cell suspension from traveling further up the inner wall of test tube 1.

Test tube 1 is rotated for a period of time such that the larger, more dense cells in the suspension are brought into contact with the inner wall of test tube 1, but unreacted reagents and most of the smaller, less dense cells and cellular debris remains within the annular cylinder of liquid 7 with inner diameter at 9a.

Normally closed solenoid valve 35 of FIG. 3 is then energized by control system 15 to connect vacuum to the interior of test tube I via effluent conduit 5 and effluent passageways 3. Liquid containing smaller, less dense cells, cellular debris and unreacted reagents is pulled through effluent passageways 3, up through effluent conduit 5, to vacuum accumulator 36, through vacuum pump 38, and out to waste reservoir 39. As shown in FIG. 2, effluent conduit 5 is formed by the inner diameter of rotating spindle 2, and the outer diameter of the non-rotating vent conduit tube 25. Effluent face seal 23 seals the top of rotating spindle 2 to the non-rotating effluent housing 22.

Air passes though filter 57 and flow resistor 56 of FIG. 5, though vent housing 24, and down to the interior of test tube through vent conduit 33. As shown in FIG. 2, vent conduit 33 is defined by the inner diameter of non-rotating vent conduit tube 25, and by the outer diameter of non-rotating wash tube conduit 28. The vent conduit tube 25 is supported at its discharge end by bearing and sealed by seal in spindle 2. Vent conduit 33 is sealed against atmosphere by upper vent conduit seal 27, and lower vent conduit seal 26. The air flowing through vent conduit 33 replaces the liquid pulled from test tube 1 via vacuum system 13. Liquid flows from test tube 1 through effluent conduit 5 until the inner diameter of the annular cylinder of liquid moves from 9a to 9b. At this point, vacuum system 13 begins to pull air provided by vent conduit 33, through effluent passageways 3. The air is then pulled into effluent conduit 5 and from there to vacuum accumulator 36 and finally to waste reservoir 39. Since there is very little pressure drop in effluent passageways 3 and effluent conduit 5, the vacuum in test tube 1 approaches the value in the vacuum accumulator 36.

The annular volume defined by diameter 9b is typically half to one-tenth of the volume defined by diameter 9a, which will result in a desirable increase of cell concentration in the washed suspension compared to the initial unwashed suspension.

While the test tube 1 is rotating, and after the annular volume in test tube 1 has been reduced to that defined by diameter 9b, solenoid valve 47 of FIG. 4 is opened by control system 15 while solenoid valve 35 of FIG. 3 remains opened so that wash fluid is drawn by vacuum pump 38 from wash fluid reservoir 46, through wash fluid conduit 8, and into test tube 1, FIG. 4 illustrates the wash fluid supply system of the present invention. This Figure is an expanded view of item 14 shown in FIG. 1. The wash fluid flows in virtually a solid stream from the lower tip of wash fluid conduit tube 28 to the bottom of test tube 1.

The inner diameter 9b of the annular cylinder of liquid moves slightly toward the center of test tube 1 due to the addition of wash fluid. When effluent passageways 3 become blocked by the inward movement of the liquid, air flowing into test tube 1 through vent conduit 33 raises the pressure within test tube 1, while the vacuum within effluent conduit 5 remains substantially constant. This creates a pressure differential across effluent passageways 3. When sufficient pressure differential is created across effluent passageways 3 to overcome the pressure created by centrifugal force on the liquid in effluent passageways 3, the liquid flows out through effluent conduit 5. Air provided by air supply 30 thus purges passageways 3 and effluent conduit 5 of liquid, and the vacuum within test tube 1 again increases. The inner diameter 9b of the annular cylinder of liquid again decreases due to the inflow of wash fluid. This cycle is repeated as long as wash fluid is being supplied by wash fluid conduit 8, vacuum is being applied to effluent conduit 5, and air flows via vent conduit 33.

The volume of liquid removed in each cycle and the length of each cycle is dependent on the size of flow resistor 48, the size of flow resistor 56, the vacuum level in vacuum accumulator 36, and the rotational speed of spindle 2. To control the vacuum level in vacuum accumulator 36, vacuum sensor 37 senses the vacuum in the vacuum accumulator 36. The vacuum control electronics 40 compares the vacuum in the vacuum accumulator 36 to a preset reference level, and controls the power provided to vacuum pump 38 to maintain the desired vacuum.

It is desirable to limit the volume of liquid associated with each cycle to a few percent of the volume of the annular volume of liquid defined by diameter 9b in order to provide an exact and reproducible volume of liquid remaining in test tube 1 at the end of the wash cycle.

The dilution of unbound reagent by the present invention is not limited by the size of the test tube, whereas the dilution of unbound reagent by conventional centrifugation is limited by the size of the test tube. In the present invention, fluid containing unbound reagent is displaced by the wash fluid, and a laminar flow velocity profile is established within liquid annulus 7 with zero velocity at the test tube wall, and maximum upward velocity at the inner diameter of the annulus 9b. In the absence of diffusion and mixing, the only unbound reagent remaining after a wash cycle is contained within a wedge shaped annulus whose lower width is zero, and whose upper width is defined by the distance between the inner wall of test tube 1 and the circle at which the upward velocity is just sufficient to reach effluent passageways 3 during the wash cycle.

For example, if the initial cell suspension is 1.0 ml, the final cell suspension is 0.5 ml, wash fluid is supplied at 1.0 ml/sec for 15 sec, the height of annulus 7 is 2.0 cm, and the diameter of test tube 1 is 1.0 cm, the average upward velocity of fluid will be 4.0 cm/sec. At a point 0.00125 cm from the test tube wall, the velocity will be 0.13 cm/sec, which is the minimum velocity required to reach the effluent passageways during the wash cycle. The volume of fluid contained in this wedge shaped annulus is 0.0039 ml, hence the dilution of the unbound reagent by the present invention is 120×, and the cell concentration factor is 2×.

With conventional centrifugation, with the same 1.0 ml initial and 0.5 ml final volumes, and assuming a remaining volume of 0.1 ml of liquid after centrifugation and removal of supernatant, the dilution is only 5× and the cell concentration factor is 2×.

After sufficient wash time has elapsed, the rotational speed of spindle 2 may be reduced to increase the final suspension volume of the sample. At reduced rotational speeds, the suspension volume changes shape from an annulus with inner and outer cylindrical walls to an annulus with an outer cylindrical wall and an inner parabolic wall. Wash fluid continues to be introduced during this period.

After sufficient wash time has elapsed, solenoid valve 47 of FIG. 4 is closed, and the wash fluid flow is halted. Solenoid valve 49 is then opened briefly to allow air to enter test tube 1 through filter 60, flow resistor 50, and wash fluid conduit 8 in order to purge wash fluid conduit 8 of wash fluid. Motor 6 is then rapidly stopped by system controller 15. Since fluid annulus 7 continues to rotate relative to the test tube wall, cells at the wall of test tube 1 are flushed from the wall and are thereby resuspended. A suitable surfactant in the wash fluid may reduce the adherence of cells to the interior wall of test tube 1, and aid in the resuspension of cells.

Preferably the surfactant is one which reduces the adhesion of particles to the receptacle and is suitable for use with biological cells (e.g. BASF Wyandotte PLURONIC-F68., P-106 used at a final concentration of 100–1000 ppm, weight/volume). In addition, motor 6 may then be rapidly accelerated and decelerated one or more times to more completely remove cells from the inner wall of test tube 1.

The motor 6 is then stopped, solenoid valve 35 is closed. Actuator 12, then raises spindle 2 via spindle support 21. As the spindle 2 is being raised, retaining member 17 holds test tube 1 down, to separate it from the spindle 2. Before spindle 2 is completely removed from test tube 1, the spindle may be rotated at a low speed to remove any liquid which may be adhering to the bottom end of the spindle. This will promote more fluid and cell recovery and reduce sample carryover effects. After spindle 2 is fully disengaged from test tube 1, carousel 29 is rotated to bring another test tube into position for cell washing.

We claim:

1. A method of replacing contaminated liquid in a particle suspension with uncontaminated liquid, said particle suspension containing first particles having a first sedimentation velocity and second particles having a second sedimentation velocity, said first sedimentation velocity being greater than said second sedimentation velocity, comprising the steps of:

a. placing a predetermined fixed volume of a contaminated particle suspension in a test tube shaped receptacle;

b. placing the receptacle on a resilient stopper, said stopper having multiple integrated conduits, the stopper so positioned as to enclose within said receptacle the contaminated particle suspension and a volume of air;

c. rotating the receptacle about an axis of symmetry with a predetermined RPM and time duration so that particles with a greater sedimentation velocity are driven by centrifugal force to an interior wall of the receptacle but with insufficient RPM and time duration for most particles having a lesser sedimentation velocity to have reached the interior wall of the receptacle;

d. introducing an uncontaminated liquid at a predetermined flow rate into the receptacle at a bottom of the receptacle and at substantially the axis of rotation of the receptacle;

e. allowing the uncontaminated liquid to flow over the particles located at an interior wall of the receptacle and displace the contaminated liquid containing said second particles towards the stopper;

f. removing the contaminated liquid from the receptacle through said conduits in the stopper;

g. delivering the removed contaminated liquid to a waste container;

h. stopping the flow of uncontaminated liquid into the receptacle and stopping the flow of contaminated liquid out of the receptacle resulting in a predetermined volume of uncontaminated liquid and the particles remaining in the receptacle; and i. resuspending the particles in the receptacle with the uncontaminated liquid.

2. The method of claim 1 wherein the particles are biological cells and the contaminated liquid comprise dissolved reagent chemicals and cellular debris.

3. The method of claim 2, wherein the particles are white blood cells.

4. The method of claim 1, wherein steps b through i are controlled by an automatic controller which operates automatically once initiated.

5. The method of claim 4, wherein step b is effected automatically and removal of the receptacle from the stopper after step i is effected automatically by an actuator controlled by the same automatic controller.

6. The method of claim 1, whereby the RPM of the receptacle is controlled in step h to regulate the-final volume in the receptacle.

7. The method of claim 1, wherein step i is effected by stopping the receptacle rotation.

8. A method of removing a substantial portion of liquid in a particle suspension said particle suspension containing first particles having a first sedimentation velocity and second particles having a second sedimentation velocity, wherein said first sedimentation velocity is greater than said second sedimentation velocity, comprising the steps of:

a. placing a predetermined volume of the particle suspension in a test tube receptacle;
   b. placing the receptacle on a solid, resilient stopper so positioned as to retain all of the particle suspension and a volume of air within said receptacle;
   c. rotating the receptacle about an axis of symmetry at a predetermined RPM for a time duration whereby most of said first particles are driven by centrifugal force to an interior wall of the receptacle, but with insufficient RPM and time duration for most less of said second particles to reach the interior wall of the receptacle; and
   d. introducing an uncontaminated liquid at a predetermined flow rate into the receptacle near a receptacle bottom and at substantially the axis of rotation of the receptacle;
   e. allowing the uncontaminated liquid to flow over the particles located at an interior wall of the receptacle and displace contaminated liquid containing said second particles towards the stopper; and
   f. removing the contaminated liquid from the receptacle through conduits in the stopper.

9. The method of claim 8 wherein further includes the steps of g) delivering the removed contaminated liquid to a suitable waste container or location;

h) stopping the flow of uncontaminated liquid into the receptacle and stopping the flow of contaminated liquid out of the receptacle resulting in a volume of uncontaminated liquid and particles remaining in the receptacle; and
   i) resuspending the particles in the receptacle the uncontaminated liquid by stopping the rotation of the receptacle resulting in the still rotating liquid scouring the particles off the surface of the non-rotating receptacle.

10. The method of claim 8, whereby step f includes creating a vacuum in said receptacle through said conduits in the stopper while said receptacle is rotating.

11. The method of claim 8, whereby step d includes combining a surfactant with the uncontaminated liquid prior to introducing the liquid into the receptacle for the purpose of reducing the adhesion of particles to the interior wall of the receptacle.

12. The method of claim 11, wherein the surfactant is suitable for use with biological cells.

* * * * *